(12) United States Patent  (10) Patent No.: US 6,306,151 B1
Lary                       (45) Date of Patent:   Oct. 23, 2001

(54) BALLOON WITH RECIPROCATING STENT INCISOR

(75) Inventor: Banning G. Lary, Miami, FL (US)

(73) Assignee: Interventional Technologies Inc., San Diego, CA (US)

( * ) Notice: Subject to any disclaimer, the term of this patent is extended or adjusted under 35 U.S.C. 154(b) by 0 days.

(21) Appl. No.: 09/280,494

(22) Filed: Mar. 30, 1999

Related U.S. Application Data

(60) Provisional application No. 60/080,094, filed on Mar. 31, 1998.

(51) Int. Cl.$^7$ .................................................. A61B 17/22
(52) U.S. Cl. ........................ 606/159; 604/96.01; 606/171
(58) Field of Search ................................ 606/1, 159, 167, 606/170, 171; 604/96.01, 19, 22, 103.04, 103.06, 103.08, 103.14; 623/1.1

(56) References Cited

U.S. PATENT DOCUMENTS

| | | | |
|---|---|---|---|
| 5,196,024 | * | 3/1993 | Barath .................................. 606/159 |
| 5,336,234 | * | 8/1994 | Vigil et al. ........................... 606/159 |
| 5,556,405 | * | 9/1996 | Lary .................................... 606/159 |
| 5,713,913 | * | 2/1998 | Lary et al. ............................ 606/159 |
| 5,797,935 | * | 8/1998 | Barath .................................. 606/159 |
| 5,902,263 | * | 5/1999 | Patterson et al. .................... 606/159 |
| 5,919,200 | * | 7/1999 | Stambaugh et al. ................. 606/159 |

* cited by examiner

*Primary Examiner*—Glenn K. Dawson
(74) *Attorney, Agent, or Firm*—Michael E. Klicpera

(57) ABSTRACT

A medical instrument which is insertable into a vascular system to incise a stent embedded within a stenosis is provided herein and includes a multi-luminal catheter with a distal expandable balloon mounted with a reciprocating cutting member. The cutting member is selectively activated by an external reciprocating mechanism which is transmitted through the catheter to the cutting member mounted on the balloon's surface. The cutting member is designed to have the characteristics necessary to cut the metallic struts of a stent. In operation, the device is placed within the stenosis having an embedded stent and the expandable balloon is inflated. Preferably, the cutting member will be facing the myocardium. Then reciprocating motion is activated and the cutting member proceeds to sever the struts of the stent and make an incision in the stenosis. It is anticipated that more than one cutting member may be mounted on the balloon's surface.

22 Claims, 3 Drawing Sheets

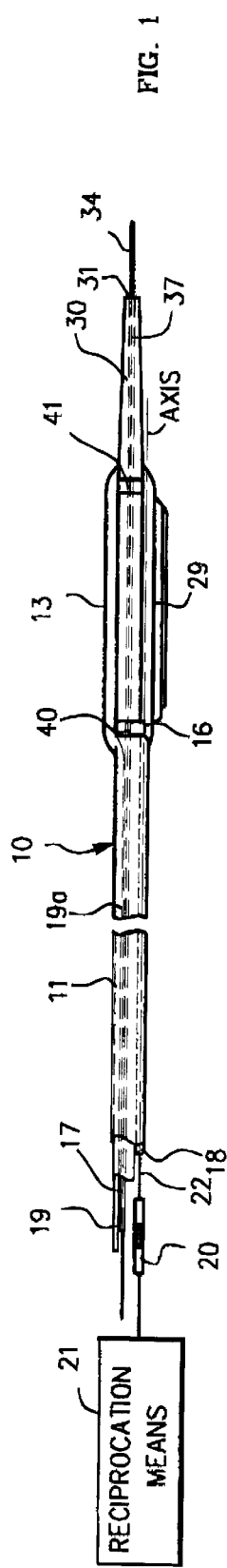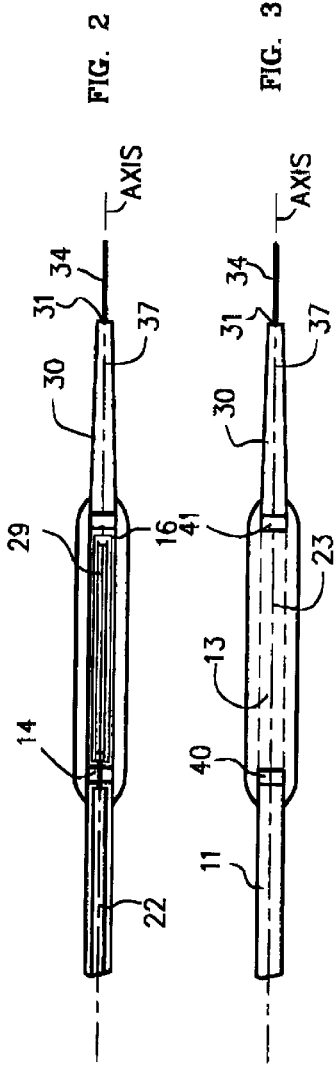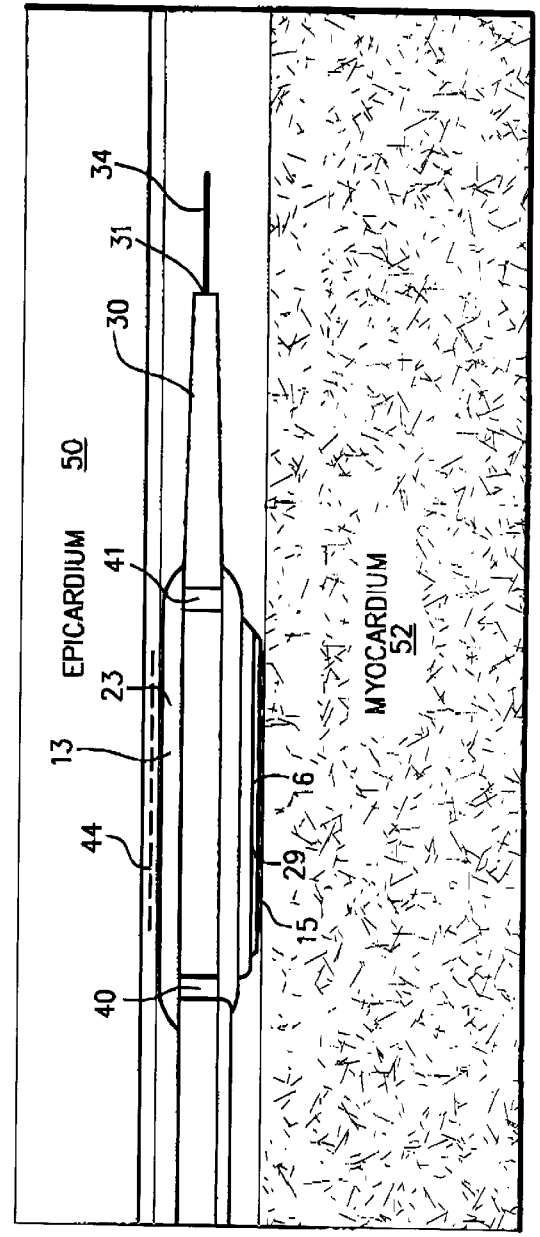

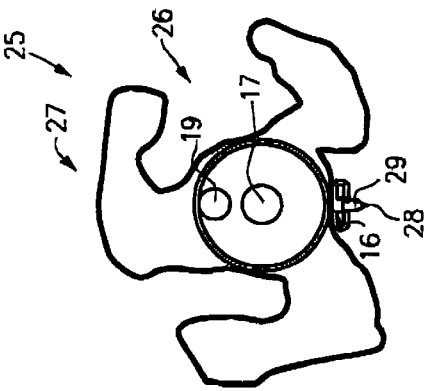
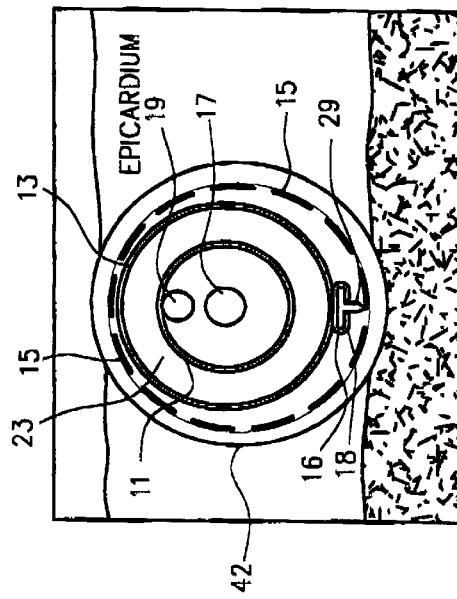
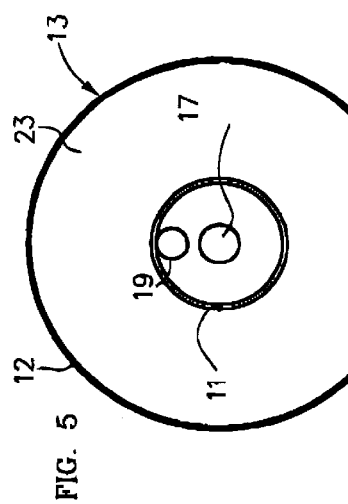
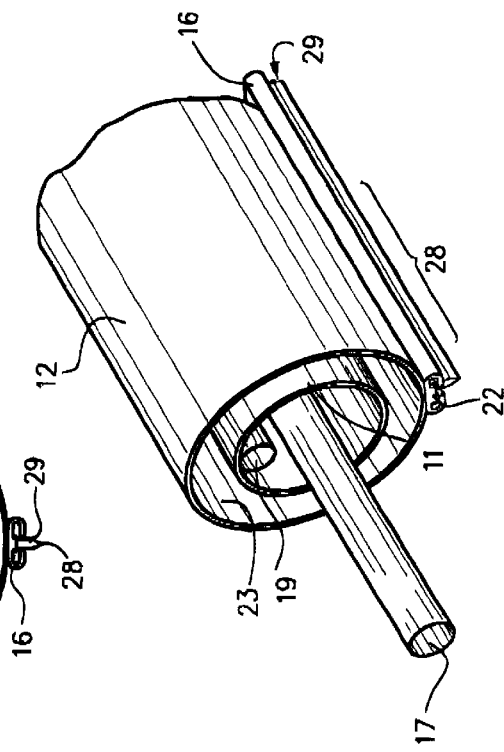

BALLOON WITH RECIPROCATING STENT INCISOR

RELATED APPLICATIONS

In accordance with 35 U.S.C. 111, a provisional patent was filed by inventor Banning Lary on Mar. 31, 1998 for a device named "Balloon with Reciprocating Stent Incisor". The U.S. PTO assigned Ser. No. 60/080,094 to this application.

FIELD OF THE INVENTION

The present invention pertains generally to medical devices for reducing the flow restriction caused by a stenosis in an artery. More specifically, the present invention relates to devices for incising the struts of a stent embedded within an arterial stenosis. The present invention is particularly, but not exclusively, useful for longitudinally incising the stent within the arterial stenosis prior to and in conjunction with standard angioplasty.

BACKGROUND OF THE INVENTION

It is well known that any significant reduction or restriction in the flow of blood through the arteries of the body can cause complications which may have serious ischemic consequences. Arterial blockages caused by plaque and fibrotic stenosis in coronary arteries are known to be a leading cause of heart attacks, subsequent strokes, and other debilitating maladies. Accordingly, it is extremely important for the health of a patient that any stenosis, or blockage, which is causing such a condition, be eliminated or reduced.

With the advent of bypass surgery techniques commonly known as CABG, the ischemic consequences of blockages in arterial segment can be alleviated by grafting around the lesion site a replacement means, typically with a saphenous vein graft. In this manner, blood is allowed to bypass the blockage in the affected artery and the blood supply to the body tissues downstream from the blockage is thereby restored. While bypass surgical procedures have become relatively safe, reliable, and effective, portions of the body must nevertheless be opened to accomplish the surgery. In other words, bypass surgery is invasive, and can consequently require significant post-operative recovery time. To avoid the drawbacks associated with invasive bypass surgery, less invasive surgical procedures have been developed wherein a device is inserted into the bloodstream of a patient and advanced into an artery to reduce or remove an arterial stenosis.

One well known and frequently used procedure to accomplish this task is popularly known as angioplasty. For a basic angioplasty procedure, a dilating balloon is positioned across the particular stenotic segment and the balloon is inflated to open the artery by breaking up and compressing the plaque which is creating the stenosis. The plaque, however, remains in the artery and is not removed. Unfortunately, in some cases, it appears that the plaque which remains in the artery may still present a stenosis. Furthermore, in approximately 30–60% of the vessels treated by angioplasty, there is a restenosis. This high recurrence rate is thought to be the result of fibrotic contraction in the lumen of the vessel.

A further alternative treatment method involves percutaneous, intraluminal installation of one or more expandable, tubular stents or prostheses in sclerotic lesions. Stents or prostheses are known in the art as implants which function to maintain patency of a body lumen in humans and especially to such implants for use in blood vessels. They are typically formed from a cylindrical metal mesh which expand when internal pressure is applied. Alternatively, they can be formed of wire wrapped into a cylindrical shape. The present invention relates to an improved stent design which by its specifically configured struts can facilitate the deployment and embedment of the stent within a vessel and is constructed from a manufacturing process which provides a controlled and superior stress yield point and ultimate tensile characteristics.

Stents or prostheses can be used in a variety of tubular structures in the body including, but not limited to, arteries and veins, ureters, common bile ducts, and the like. Stents are used to expand a vascular lumen or to maintain its patency after angioplasty or atherectomy procedures, overlie an aortic dissecting aneurysm, tack dissections to the vessel wall, eliminate the risk of occlusion caused by flaps resulting from the intimal tears associated with primary interventional procedure, or prevent elastic recoil of the vessel.

These metallic stents are deployed inside an arterial segment and embedded in the vessel to maintain patency typically after angioplasty or atherectomy interventions. Once they are so positioned, they are extremely difficult to remove. Often the vessels in which they are placed become occluded or severely restenosed in a relative short period of time. These complications continue to occur the longer the stents remain in place, resulting in total or partial obstruction of blood flow through the artery. Usually, the distal portion of the artery will remain patent and is supplied by collateral circulation through branches of other major arteries. However, tile decreased direct blood flow results in many cardiac problems.

It has also been shown that when an angioplasty procedure is performed after the stenotic segment is longitudinally incised, the opening established through the segment is much larger as compared to standard angioplasty without the prior incisions. Still further, the increase in the opening in the stenotic segment is accomplished without tearing the vessel wall. Moreover, it has been found that incising the stenosis prior to dilation allows greater compression of the stenotic tissue with decreased likelihood of the stenosis rebuilding at a later date. As those skilled in the art will appreciate, the plaque creating a common arterial stenosis is somewhat fibrous and will tend to return to its original predilation configuration. With this fibrous composition, the stenosis is therefore more likely to maintain a compressed configuration if the fibers are incised prior to balloon dilation. On the other hand, if the fibers in the stenosis is not incised first, the completeness of the compression of the stenosis is dependent on whether the inflated balloon is able to break apart fibers in the tissue as those skilled in the art will recognize, dilation of a segment is of course limited by the arteries able to withstand dilation. Over-dilation can have the catastrophic result of rupturing the vessel.

In light of the above, it is an object of the present invention to provide an improved device and method for cutting a previously deployed and embedded stent within an arterial stenosis and additionally longitudinally incising the stenotic segment to enhance blood flow.

It is another object of the present invention to provide a cutting device which, in cooperation with an angioplasty procedure, is able to produce an opening in a stenotic segment where the diameter of the opening is greater than the insertion diameter of the device.

It is also an object of the present invention to provide a device which allows improved control over the length of the incisions produced in the stenotic segment Yet another object of the present invention is to provide a device which is flexible enough to allow advancement of the device through narrow vessels and around sharp turns.

Still further, it is an object of the present invention to provide a device for longitudinally incising a stenotic segment of an artery which is relatively easy to manufacture and is comparatively economical.

SUMMARY OF THE INVENTION

As previously discussed, stents are placed inside arterial segments to maintain patency typically after angioplasty or atherectomy interventions. Once they are positioned, they are extremely difficult to remove. Often the vessels in which they are placed become occluded or severely restenosed in a relative short period of time. These complications continue to occur the longer the stents remain in place, resulting in total or partial obstruction of blood flow through the artery. Usually, the distal portion of the artery will remain patent and is supplied by collateral circulation through branches of other major arteries. However, this decreased direct blood flow results in many cardiac problems.

Published laboratory experiments demonstrate it is possible to cut the inside of a coronary artery longitudinally with immediate and continued blood flow. A new anatomical vessel evolves which consists of a portion of the original arterial wall and a new portion which is in continuity with the original arterial wall. A lining (intima) of the With this knowledge it is possible to devise an instrument which will cut through the metallic strands of the stent and through the vessel wall of the narrow occluded artery. The artery can then be further decompressed from within by angioplasty to form the aforementioned vessel. This permits blood to flow directly to the distal vessel and its branches.

All instruments which would be capable of performing the above described procedure is the basis for this invention. It consists, in general, of a delivery catheter, an angioplasty balloon, and a cutting member or a reciprocating abrasive member which transacts the struts of the metallic stent.

Reference to the illustrations and accompanying text will elucidate the components which form the apparatus and the mechanism of action.

The catheter is multi-lumen design, the first lumen contains a guide wire, the second contains a transmitting member, and the third lumen conveys fluid or gas to expand the distal balloon. The balloon is fixedly attached at both ends to the catheter but in fluid communication with the inflation/deflation lumen of the catheter. Fixedly attached to the periphery of the balloon is a retaining member. Engaged and slidably attached to the retaining member is an abrasive member designed to cut through the struts of stents. A transmitting member, transcending the longitudinal length of the catheter with a lumen, is fixedly attached to the distal end of the abrasive member with the proximal end of the transmitting member attached to a reciprocating apparatus. The transmitting member is made of a strong, yet flexible material. The abrasive member, which is slidably attached to the retaining member, is constructed in a manner which permits reciprocal motion of the abrasive member, but remains contained within the retaining member. The retaining member includes constraints comprising of detents that are provided to prevent the escape of the abrasive member through the either end of the retaining member.

The catheter, which has a distally located folded balloon to which peripherally attached are the retaining member and the abrasive member, is passed within a larger introductory catheter, commonly known as a guiding catheter, to the base of the aorta where the guide wire is passed through the coronary vasculature of the target coronary artery and past the area of the embedded stent. The catheter is passed over the guide wire through the area of the embedded stent, so that the balloon approximates the segment containing the stent.

At that site the balloon is expanded which exposes the abrasive member, and approximates it against the tissue containing the stent. The reciprocating apparatus is activated to transmit a reciprocating action to the transmitting member which is contained almost totally within the small channel within the catheter. The force and length of movements of the transmitting member are only slightly decreased (dampened) since it is moveably contained within the transmitting channel. The stent is cut by the filing action of the abrasive member while the balloon is progressively expanded to permit cutting of all of the metallic struts of the stent and to effect a new angioplasty. The apparatus may be constructed with the abrasive member on two or more sides of the balloon so the stent would be cut at two or more places opposite to each other, thus creating a bivalve and decompressing effect.

During the procedure, distal blood flow with tamponading of the transacted segment could be achieved by combining the retaining member and the abrasive member with a perfusion sleeve or apparatus as disclosed in patent Ser. No. 09/221,801 filed with the PTO on Dec. 28, 1998.

BRIEF DESCRIPTION OF THE DRAWINGS

FIG. 1 is a perspective view of the balloon catheter with reciprocating stent cutting incisor demonstrating the multi-lumen catheter body containing a guide wire, a transmitting member and a inflation/deflation port. Also shown is the expandable balloon mounted with a retaining member/abrasive member assembly on one side of the balloon. Engaged to the transmitting member is a reciprocation means.

FIG. 2 is a partial cross-sectional bottom view of the balloon catheter with reciprocating stent cutting incisor demonstrating a more detailed view of the retaining member with abrasive member engaged to the transmitting member located within one of the lumens of the catheter.

FIG. 3 is a partial cross-sectional top view of the balloon catheter with reciprocating stent cutting incisor demonstrating a more detailed view of the relative position of the expandable balloon portion of the catheter.

FIG. 4 is a perspective view of the balloon catheter with reciprocating stent cutting incisor demonstrating the proper orientation of the device with the expandable balloon portion engaging the vessel wall in close proximity to the epicardium and the abrasive member engaging the vessel wall in close proximity to the myocardium.

FIG. 5 is a cross-sectional view of the balloon catheter with reciprocating stent cutting incisor demonstrating the multi-lumen catheter with balloon assembly in an expanded configuration. Mounted on the surface of the balloon is a retaining member containing the abrasive member.

FIG. 6 is a cross-sectional view of the balloon catheter with reciprocating stent cutting incisor demonstrating the multi-lumen catheter with balloon assembly in a contracted configuration. Mounted on the surface, yet positioned within a protective valley of the balloon, is a retaining member containing the abrasive member.

FIG. 7 is a partial cross-sectional view of the balloon catheter with reciprocating stent cutting incisor demonstrating a more detailed view of the physical relation between the catheter, expandable balloon, retaining member, abrasive member, and the multi-luminal structure of the catheter.

FIG. 8 is a cross-sectional view of the balloon catheter with reciprocating stent cutting incisor in an arterial segment having an embedded stent. The abrasive incisor is engaged to one of the struts of the stent and positioned towards the myocardium.

DESCRIPTION OF THE PREFERRED EMBODIMENT

Figure 9:
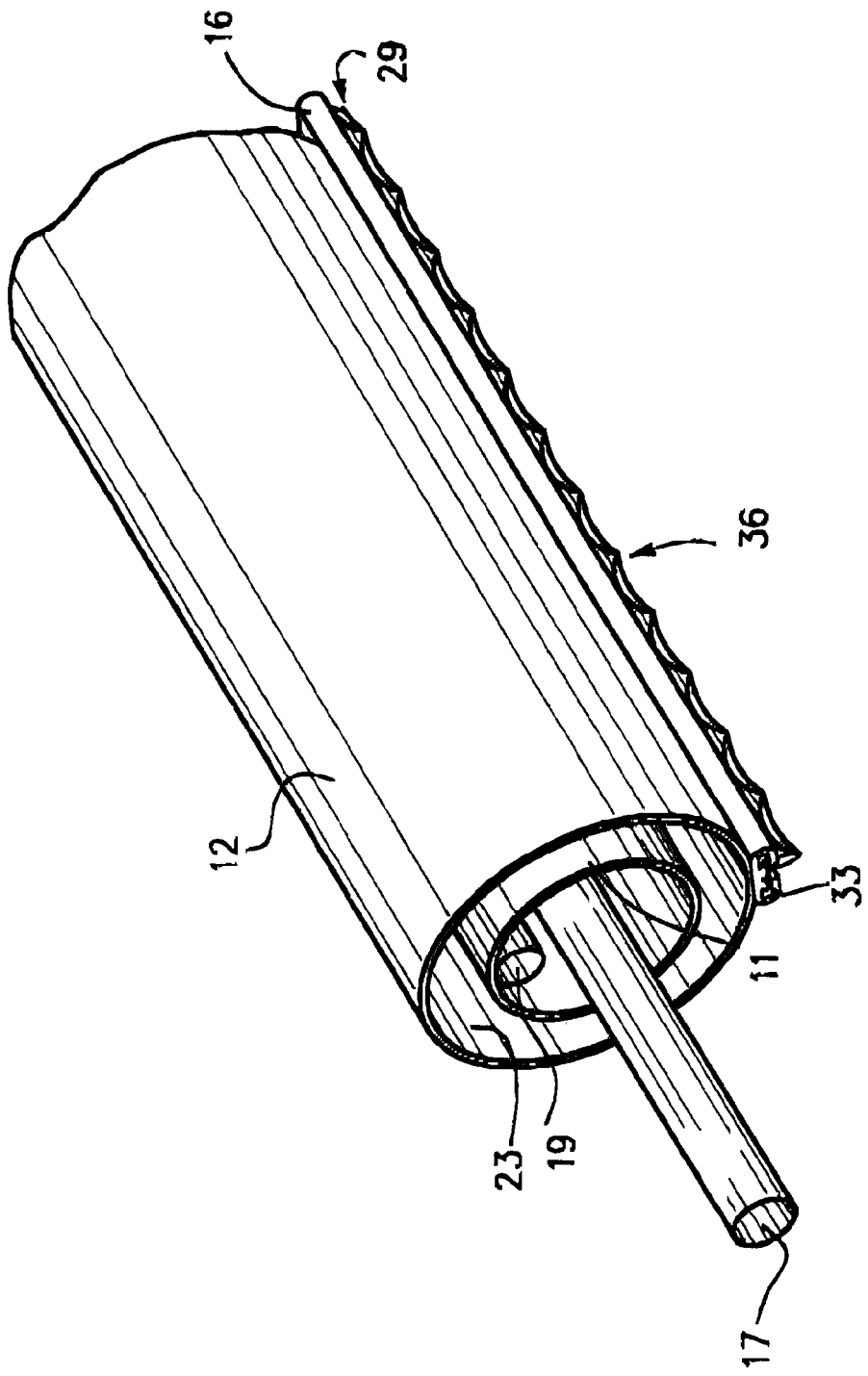
FIG. 9 is a partial cross-sectional view of the balloon catheter with reciprocating stent cutting incisor demonstrating a more detailed view of the physical relation between the catheter, expandable balloon, retaining member, abrasive member with teeth, and the multi-luminal structure of the catheter.

Referring initially to FIG. 1, the stent cutting device of the present invention is shown and generally designated number 10. FIG. 1 demonstrates that the stent incisor apparatus 10 comprises a catheter 11, designed to function with a standard guide wire 34, an expandable angioplasty type balloon 13 affixed to the distal end of catheter 11. Extending along the longitudinal length of the catheter 11 and within a transmitting lumen 18, is a transmitting member 22 which is permanently attached to an abrasive member 29 held in containment by retaining member 16. The transmitting member 22 reciprocates in a line parallel to or along the longitudinal axis of the catheter and is non-permanently engaged to a reciprocating apparatus. Such engagement techniques are commonly know in the art and includes various threading techniques, press fit, or other locking mechanisms. Such reciprocating apparatus are also commonly known by the artisan. For example, some electric shavers utilized a simple mechanism that employs a reciprocating means to move one cutting screen in relation to another cutting screen to achieve the desired cutting. Such technology could be adapted to function as the reciprocating means for the present invention.

The catheter 11 also has a guide wire lumen 17 generally extending along the longitudinal length of the catheter 11 for which a guide wire 34 is of sufficient size to slidably accommodate a standard guide wire. In an alternate embodiment, the guide wire lumen could be limited to a short distal section yielding a rapid exchange design. Typically, the guide wire is first inserted into the arterial system of a human subject in the customary manner. Then, by inserting the guide wire into lumen 17, the stent cutting device 10 is threaded through an insertion catheter into the femoral artery and advanced through the arterial system to the stenotic segment.

The catheter 11 also has a typical inflation/deflation lumen 19 that is in fluid communication with balloon lumen 23. Lumen 19 is of sufficient size to act as a fluid conduit for the balloon catheter. The infusion of contrast/saline solutions through this lumen functions to expand the balloon and conversely, the withdraw of this solution through the lumen acts to contract the balloon. All three lumens, the transmitting lumen 18, the guide wire lumen 17 and the balloon inflation/deflation lumen 19 can exist completely independent of each other and contained within the catheter shaft. Alternately, lumens 18 and 17 can be positioned coaxially within inflation/deflation lumen 19. The three lumens of the catheter all extend from the proximal end of the catheter to various locations within the distal expandable balloon section. Lumen 17, which contains the guide wire, terminates at the distal end 31 of the tapered tip 30. Lumen 18, which contains the transmitting member, terminates just proximal to the balloon at a transition joint 14. Lumen 19, which conveys fluid or gas to expand and contract the balloon 13, extends to a position within the balloon where it has one or more ports that are in communication with the balloon's expandable lumen 23.

The construction of the catheter follows the teaching of Briggs et. al. U.S. Pat. No. 4,263,236 and modifications and improvements subsequently used in common angioplasty apparatuses. The expandable balloon 13 is fixedly attached at both ends to the catheter 11. To the periphery of the balloon 13, fixedly attached is the retaining member 16, to which is slidably attached the abrasive member 29. The transmitting member 14 is fixedly attached at the distal end to the abrasive member 29 and at its proximal end it is attached to a transmitting member 23 which is ultimately connected to a reciprocating apparatus 20. The transmitting member is made of a strong flexible material. The retaining member 16 is fixedly attached to the balloon 13. The abrasive member 29 is slidably attached to the retaining member 16, which is constructed in a manner which permits motion of the abrasive member 29, but with constraints determined by distal detent 33, and proximal detent 32 which also prevent the escape of the abrasive member 29, through either end of the retaining member 16.

Referring now to FIGS. 2 and 3, the distal end of the catheter 11 is shown. Generally, FIG. 2 is a bottom perspective view of the reciprocating stent cutting incisor demonstrating a more detailed view of the abrasive member 29 positioned within retaining member 16. Also shown is a tapered distal tip 30 having a distal opening 31 with protruding guide wire 34. The proximal section of the balloon/retaining member/abrasive/member assembly shows the catheter 11 and internally located transmitting member 22. The abrasive member 29 is fixedly engaged to the transmitting member 22 located within the transmitting lumen of the catheter 11 by means of a transition joint 14. The abrasive member 29 is slidably engaged to the retaining member 16 such that the abrasive member can move back and forth, or distally and proximally in a line or direction parallel to the longitudinal axis of the catheter as guided by transmitting member 22. Abrasive member 29 is preferably fabricated from a metallic material and having an abrasive narrowed edge 28 extending radially from the catheter. It is well known in the art to employ those methods necessary to fabricate a metallic blade with an abrasive narrowed edge 28 with the capability to sever or cut a metal object, such as the struts 15 of a stent while at the same time also have the ability to maintain the strength and integrity of the edge 28 and abrasive member 29 to resist any damage that might occur during the cutting operation. It is also anticipated that the abrasive member 29 can be hardened to achieve the desired characteristics of strength and integrity. Furthermore, the edge 28 of the abrasive member can be formed with teeth in various configurations to facilitate the cutting of the metallic struts 15 of the stent. It is also anticipated by the inventor that the abrasive member 29 can be fabricated from a non-metallic material, such as a rigid polymer. Furthermore, the rigid polymer can be fitted by adhesive or other means with sharpened abrasive metallic, diamond, or ceramic teeth or edge. FIG. 3 demonstrates a top perspective view of the catheter with reciprocating stent cutting incisor showing a more detailed view of the relative position of the expandable balloon 13 portion of the catheter. The extent of the reciprocating cutting motion of the abrasive member 29 is indicated by a proximal 40 and distal 41 radio-opaque marker. The catheter shaft 1, not shown as a cross-sectional view as in FIG. 2, is fixedly attached to the proximal portion of the expandable balloon 13. The distal tapered tip 30 of the balloon is formed with an opening 31 which allows the guide wire 34 to exit.

Referring now to FIG. 4, the stent cutting device of the present invention is shown inserted into the arterial system of a human in the customary manner. Typically, device 10 is inserted through an insertion catheter (not shown) into the femoral artery and advanced through the arterial system to the stenotic segment. FIG. 4 is a perspective view of the balloon catheter with reciprocating stent cutting incisor demonstrating the proper orientation of the device with the expandable balloon portion engaging the vessel wall in close proximity to the epicardium having a inner intimal vessel wall boundary 44 and the abrasive member engaging the vessel wall in close proximity to the myocardium. Shown are the struts 15 of the stent near the myocardium 52 that are to be severed by the present invention and on the opposite side are the struts 15 of the stent near the epicardium 50. Also shown is the tapered distal tip 30 with exiting guide wire 34. The extent of the reciprocating cutting motion of the abrasive member 29 is indicated by a proximal 40 and distal 41 radio-opaque marker. The method of application of the catheter 1, to which is attached the folded balloon 13, to which are attached the retaining member 16, and the abrasive member 29, is passed within a larger introductory catheter (not shown) to the base of the aorta where the guide wire 34 is passed down the target coronary artery past the area of the embedded struts of stent 15. The catheter is passed over the guide wire through the area of the stent, so that the balloon 13 approximates the segment containing the stent.

At that site, the balloon 13, is expanded, which exposes the abrasive member 29, and approximates it against the tissue containing the struts of the stent 15. The reciprocating apparatus 21 is activated to transmit a reciprocating action to the transmitting member 22, which is contained almost totally within the small lumen 18. The force and length of movements of the transmitting member 14 are only slightly decreased (dampened) since it is moveably contained within the transmitting lumen 18. The struts of the stent 15 are cut by the filing action of the abrasive member 29, while the balloon 13 is progressively expanded to permit cutting of all of the metallic struts of the stent 15, and to effect a new angioplasty. The apparatus may be constructed with the abrasive member 29 on two or more sides of the balloon so the struts of the stent 15 would be cut at two or more places.

During the procedure, distal blood flow with tamponading of the transacted segment could be achieved by combining the retaining member 16 and the abrasive member 29 with a perfusion device.

Referring now to FIG. 5, the cooperation between the balloon, the retaining member, and the abrasive member can be more clearly seen. In the preferred embodiment, the abrasive member comprises a base portion and a vertical portion, somewhat resembling a "T". The retaining member 16 is configured to have a channel which slidably accepts the base portion of the abrasive member and positions the vertical portion to face radially from the balloon's longitudinal axis. This configuration also prevents the abrasive member 29 from rotating relative to its radial projection. The length of the channel is longer than the length of the abrasive member and therefore allows the abrasive member 29 to move longitudinally a predetermined distance, this distance is approximately equal to the reciprocating distance, but prevents cutting member 29 from rotating relative to the catheter shaft 11. A detent or lug 33 is located on the distal end of the channel of retaining member 16 to inhibit the abrasive member from exiting. As shown in FIG. 2, the proximal end of the abrasive member is engaged to the transmitting member. At this cross section, only the guide wire lumen 17 and inflation/deflation lumen 19 are present; the transmitting lumen terminates at a more proximate position. The balloon, when expanded, defines an expandable balloon lumen 23 which is generally filled with a contrast/saline solution.

FIG. 6 is a cross-sectional view of the reciprocating stent cutting incisor catheter demonstrating expandable balloon in a contracted configuration. This is the insertion configuration of the device 10. In this configuration, the retaining member/abrasive member assembly is prevented from contacting the vessel wall and making unintentional incisions during insertion and placement. The expandable balloon can be folded on the surface following the teachings of Farr et. al. and Vigil. When the balloon is contracted, it folds into two or more wings or peaks 27 with protective valleys 26 existing between the peaks. Mounted on the surface 12 of the balloon 13, yet positioned within one of the protective valleys 26 of the balloon, is a retaining member 16 containing the abrasive member 29. The abrasive member 29 is moveably contained by a detent 33 within the retaining member 16.

Now referring to FIG. 7 which is a partial cross-sectional view of the balloon catheter with reciprocating stent cutting incisor, a more detailed view of the physical relation between the catheter, expandable balloon, retaining member, abrasive member, and the multi-luminal structure of the catheter is provided. Shown is the balloon in an expanded configuration with the retaining member 16 mounted on the surface 12 of the balloon. The inflation/deflation lumen 19 and guide wire lumen 17 are present in this section. In this figure, the retaining member is shaped to have a void that represents a "T" configuration which corresponds to the shape of the base and vertical portion of the brasive member 29. The outer surface of the vertical portion is a cutting edge 28. Also shown is the distal detent or lug 33 which occludes the channel of the retaining member in such a way that the abrasive member cannot escape.

Referring to FIG. 8 which provides a cross-sectional view of the balloon catheter with reciprocating stent cutting incisor 10 in an arterial segment having an embedded stent 15. The balloon 13 of the catheter 11 is at least partially expanded. The abrasive incisor is engaged to the struts of the stent 15 and positioned toward the myocardium 52. The reciprocating means 21 now can be activated to sever the struts of the stent 15. If desired, the abrasive member can continue to cut through the adventitia of the vessel 42 and in myocardium to create a new vessel in the myocardial tissue.

Finally referring to FIG. 9 which is a partial cross-sectional view of the balloon catheter with reciprocating stent cutting incisor, demonstrating a more detailed view of the physical relation between the catheter, expandable balloon, retaining member, abrasive member with teeth, and the multi-luminal structure of the catheter. Shown is the balloon in an expanded configuration with the retaining member 16 mounted on the surface 12 of the balloon. The inflation/deflation lumen 19 and guide wire lumen 17 are present in this section. In this figure, the retaining member is shaped to have a void that represents a "T" configuration which corresponds to the shape of the base and vertical portion of the abrasive member 29. The outer surface of the vertical portion of the abrasive member 29 is a cutting edge with teeth 36.

OPERATION

To use the device of the present invention, device 10 is typically inserted into the arterial system through an insertion catheter (not shown) previously inserted into the femoral artery. When inserted, device 10 is in the insertion configuration as is depicted in FIGS. 5 and 8 where the abrasive member 29 is retracted into folds of the balloon 13. Device 10 is advanced into the vessel having a previously implanted stent in a currently stenotic segment and is positioned adjacent the stenosis as is well known in the art. Once adjacent to the stenotic segment, the balloon 13 is at least partially inflated to hold the catheter stationary and engage the abrasive member 29 to the stenosis and implant stent surfaces of the instrument. Then the reciprocating means is activated to mechanically move and energize the cutting action of the abrasive member 29 in a "to-and-fro" motion as the abrasive edge 28 passes through the stenotic segment and embedded struts of the stent. This sawing action, as noted above, results in increased cutting efficiency of the metallic struts where additional cutting can be accomplished to create a newer channel. Once the incisions have been made, the stenosis is ready to be further dilated. After making incisions, the balloon 13 can be deflated and the device 10 retracted and a routine angioplasty procedure can be performed using the same guide wire.

Surgical control over the length of the incisions is also provided by the device of the present invention. In the present device, the maximum length of an incision is determined by the length of the channel of the retaining member 16. As long as the catheter 11 is maintained in a constant position, the surgeon knows the exact length of incision which is possible, and the risk of incising the artery beyond the stenosis is reduced. For long stenosis containing more than one stent, the catheter can be advanced after the initial incisions have been made. Accordingly, by alternatively incising and advancing the catheter, very long stenosis can be treated.

While the particular stent cutting incisor as herein shown and disclosed in detail is fully capable of obtaining the objects and providing the advantages herein before stated, it is to be understood that it is are merely illustrative of the presently preferred embodiments of the invention and that no limitations are intended to the details of construction or design herein shown other than as described in the appended claims. It should be noted that the apparatus would be equally applicable to areas of calcific stenosis which would be difficult to cut with a sharpened knife edge. Many methods to perform the transection of calcified or stent stenosis could be employed. These include carbide and diamond abrasives, ultrasound, lasers, and others.

What is claimed is:

1. A device insertable into a vessel for cutting a stent implanted into stenotic tissue comprising:
   a catheter including a body portion, a proximal end, and a distal end, said catheter defining a longitudinal axis and an expandable balloon at said distal end, said expandable balloon having an inner surface and an outer surface, said balloon being in fluid communication with a balloon inflation and deflation means;
   a retaining means affixed to said outer surface of said expandable balloon;
   a cutting member for incising a stent implanted in stenotic tissue comprising a transmitting shaft engaged to a cutting means, said cutting member being reciprocatable along an axis substantially parallel to said longitudinal axis, a portion of said cutting member located within said retaining means.

2. The device as recited in claim 1 wherein said expandable balloon prevents said cutting means from contacting said tissue when said expandable balloon is in a contracted configuration.

3. The device as recited in claim 1 wherein said retaining means comprises a channel with a restricting means to contain said cutting means.

4. The device as recited in claim 3 wherein said restricting means comprises a channel shaped with a void representing a "T" shape.

5. The device as recited in claim 3 further comprising a pair of detents located on terminal ends of the restricting means.

6. The device as recited in claim 1 wherein said cutting means is configured in a "T" shape.

7. The device as recited in claim 1, wherein said cutting means is fabricated from a metal.

8. The device as recited in claim 1, wherein said cutting means is fabricated from a rigid polymer.

9. The device as recited in claim 1, wherein said cutting means has one or more teeth.

10. An insertable catheter device for incising a stent implanted within a stenosis in a vessel, said device usable in conjunction with a standard guide wire, said device comprising:
    a catheter including a body portion, a proximal end, and a distal end, said catheter defining a longitudinal axis and an expandable balloon at said distal end, said expandable balloon having an inner surface and an outer surface, said balloon being in fluid communication with a balloon inflation and deflation means;
    a retaining means affixed to said outer surface of said expandable balloon;
    a cutting member for incising a stent implanted in stenotic tissue having a transmitting shaft engaged to said cutting member being reciprocatable along an axis substantially parallel to said longitudinal axis, said cutting member being located entirely within said retaining means.

11. The device as recited in claim 10 wherein said expandable balloon prevents said cutting means from contacting said tissue when said expandable balloon is in a contracted configuration.

12. The device as recited in claim 10 wherein said retaining means comprises a channel with a restricting means to contain said cutting means, said restricting means having a distal and proximal terminal end.

13. The device as recited in claim 12 wherein said restricting means comprises a channel shaped with a void representing a "T" shape.

14. The device as recited in claim 12 further comprising a pair of detents located on the terminal ends of the restricting means.

15. The device as recited in claim 10, wherein said cutting means is configured in a "T" shape.

16. The device as recited in claim 10, wherein said cutting means is fabricated from a metal.

17. The device as recited in claim 10, said cutting means is fabricated from a rigid polymer.

18. The device as recited in claim 10, wherein said cutting means has one more teeth.

19. The device as recited in claim 10, wherein said catheter includes a guide wire lumen extending along the longitudinal length of said catheter.

20. The device as recited in claim 10, wherein said catheter includes a relatively short guide wire lumen located near the distal end of said catheter.

21. A method of reducing the flow restriction resulting from a stent implanted stenosis in a vessel comprising the steps of:

inserting a guide wire in a vessel of a human being and moving said guide wire along said vessel until said guide wire has passed said stenosis;

placing a stent cutting catheter device on said wire, said catheter device comprising a body portion, a proximal end and a distal end, said catheter device also defining a longitudinal axis and having a expandable balloon at said distal end, said expandable balloon having an outer surface, said balloon being in fluid communication with a balloon inflation and deflation means, a retaining means affixed to said outer surface of said expandable balloon, and a cutting member for incising a stent implanted in stenotic tissue comprising a transmitting shaft engaged to a cutting means, said cutting member being reciprocatable along an axis substantially parallel to said longitudinal axis, a portion of said cutting member located within said retaining means;

moving said catheter device along said wire until said catheter device is adjacent said stenosis;

inflating said expandable balloon on said catheter to engage said cutting means to the stenotic tissue containing said stent;

activating a reciprocatable motion to said transmitting shaft such that said cutting means longitudinally incises said stent and said stenosis; and deflating said expandable balloon and removing said catheter device and said guide wire from said vessel.

22. The method as recited in claim 21 further comprising aligning said cutting means prior to activating said reciprocatable motion so that said cutting means is directed towards myocardial tissues.

* * * * *